(12) United States Patent
Hansen et al.

(10) Patent No.: US 12,097,376 B1
(45) Date of Patent: Sep. 24, 2024

(54) MOBILE DEFIBRILLATOR WITH IMPROVED PADS, CHARGING, AND SWITCHING

(71) Applicant: Defibrio AS, Fana (NO)

(72) Inventors: Jon Kåre Hansen, Fana (NO); Bjarte Nore, Bergen (NO); Arne Bergby, Raadal (NO); Joshua Hale, Arlington, MA (US)

(73) Assignee: Defibrio AS, Fana (NO)

( * ) Notice: Subject to any disclaimer, the term of this patent is extended or adjusted under 35 U.S.C. 154(b) by 0 days.

(21) Appl. No.: 18/302,113

(22) Filed: Apr. 18, 2023

(51) Int. Cl.
*A61N 1/39* (2006.01)
*A61N 1/04* (2006.01)
*A61N 1/05* (2006.01)

(52) U.S. Cl.
CPC ........... *A61N 1/3904* (2017.08); *A61N 1/046* (2013.01); *A61N 1/0492* (2013.01); *A61N 1/0502* (2013.01); *A61N 1/3975* (2013.01); *A61N 1/3993* (2013.01)

(58) Field of Classification Search
CPC .... A61N 1/3904; A61N 1/046; A61N 1/0492; A61N 1/0502; A61N 1/3975; A61N 1/3993
See application file for complete search history.

(56) References Cited

U.S. PATENT DOCUMENTS

| | | | |
|---|---|---|---|
| 11,173,315 B1 * | 11/2021 | Hansen | A61N 1/3987 |
| 2016/0193109 A1 * | 7/2016 | Fleischacker | A61N 1/3925 |
| | | | 601/41 |

* cited by examiner

*Primary Examiner* — Mallika D Fairchild
(74) *Attorney, Agent, or Firm* — DLA PIPER LLP (US)

(57) ABSTRACT

The disclosed systems and methods provide a mobile defibrillator system that can include a mobile defibrillator (AED) unit configured to operatively connect to a device capable of running an application. The mobile AED unit can include circuitry for administering an electric shock to a subject; and one or more pads. Each pad can include one or more needles electrically connected to the circuitry and can be configured to pierce skin of the subject; reside within the subject; and deliver current from the electrical shock to the subject.

8 Claims, 14 Drawing Sheets

MOBILE DEFIBRILLATOR WITH IMPROVED PADS, CHARGING, AND SWITCHING

BACKGROUND OF THE DISCLOSURE

Sudden cardiac arrest (e.g., heart failure) can involve the abrupt loss of heart function, breathing, and consciousness. In many cases, the condition can result from an electrical disturbance in the heart that disrupts its pumping action, which can stop blood flow within the body. In the United States alone, it is estimated that around three hundred thousand people die from cardiac arrest outside hospitals every year.

SUMMARY OF THE DISCLOSURE

According to one aspect of the present disclosure, a mobile defibrillator system can include a mobile defibrillator (AED) unit configured to operatively connect to a device capable of running an application. The mobile AED unit can include circuitry for administering an electric shock to a subject; and one or more pads. Each pad can include one or more needles electrically connected to the circuitry and can be configured to pierce skin of the subject; reside within the subject; and deliver current from the electrical shock to the subject.

In some embodiments, the one or more needles can include a metal material. In some embodiments, the one or more needles can be curved. In some embodiments, the one or more needles can be curved away from the subject. In some embodiments, the one or more needles can be configured to reside within subcutaneous tissue of the subject. In some embodiments, the one or more pads can be foldable. In some embodiments, the one or more needles can be configured to be activated in response to an indication received from the device. In some embodiments, the indication can be generated based on detecting an impedance between the one or more pads and the subject above a predefined threshold.

According to another aspect of the present disclosure, a mobile defibrillator system can include a mobile defibrillator (AED) unit configured to operatively connect to a device capable of running an application and operating as a first power source for the mobile AED. The mobile AED unit can include circuitry for administering an electric shock to a subject; one or more pads configured to adhere to the subject for administering the electrical shock; a first charging port; and a second charging port. The device, via one or more processors, can be configured to switch from the first power source at the first charging port to a second power source at the second charging port during a defibrillation procedure.

In some embodiments, the device, via one or more processors, can be configured to determine that a battery level of the first power source is below a predefined threshold; display a query on the device; in response to displaying the query, receive an indication that the second power source is nearby from a user; detect that the second power source is within a predefined vicinity; and in response to detecting that the second power source is within a predefined vicinity, initiating a power source switch process. In some embodiments, the power source switch process can include initiating a transfer of data between the device and the second power source; performing a handshake between the device and the second power source; receiving an indication that the second power source is connected to the second charging port; and continuing the defibrillation procedure.

In some embodiments, the power source switch process can include reverting to the device to power the mobile AED in response to an error. In some embodiments, detecting that the second power source is within the predefined vicinity can be performed via Bluetooth, NFC, or WiFi. In some embodiments, detecting that the second power source is within the predefined vicinity can include receiving a position, version, and a capacity of the second power source; analyzing the position, the version, and the capacity of the second power source; determining that the second power source is acceptable; and transmitting an alert to the second power source.

According to another aspect of the present disclosure, a mobile defibrillator system can include a mobile defibrillator (AED) unit configured to operatively connect to a device capable of running an application and operating as a power source for the mobile AED. The mobile AED unit can include circuitry for administering an electric shock to a subject that can include a charge controller, a sense line bias circuit; a current sense resistor, a switch, a transformer, and a capacitor; and one or more pads configured to adhere to the subject for administering the electrical shock.

In some embodiments, the charge controller can be configured to control the sense line bias circuit with a pulse width-modulated waveform. In some embodiments, the current sense resistor can be configured to monitor a current flowing through the switch and the transformer. In some embodiments, the charge controller can be configured to shut off the switch in response to the current sense resistor measuring a voltage above a predefined threshold. In some embodiments, the predefined threshold can be 78 mV. In some embodiments, a current limit of the transformer can be greater than 2 amperes.

According to another aspect of the present disclosure, a mobile defibrillator (AED) device can include a mobile AED unit configured to operatively connect to a device capable of running an application. The mobile AED unit can include one or more electrodes and can be configured to measure breathing data for a subject. The device can be configured to, via one or more processors executing on the device, detect a connection of the mobile AED unit to the device; detect that the one or more electrodes have been connected to the subject; receive EKG measurements of the subject recorded by the electrodes; receive measured breathing data from the AED unit, the breathing data associated with breathing movements of a chest of the subject; receive wearable data from a wearable device associated with the subject; analyze the breathing data to determine a breathing pattern of the subject; determine, based on the received EKG measurements, the wearable data, and the determined breathing pattern, that the subject requires an electrical shock; determine shock pattern factors based on the received EKG measurements, the wearable data and the determined breathing pattern, the shock pattern factors comprising a duration, a time interval, and an energy level; and administer the electrical shock to the subject using the determined shock pattern factors via the mobile AED based on the determining.

BRIEF DESCRIPTION OF THE FIGURES

Various objectives, features, and advantages of the disclosed subject matter can be more fully appreciated with reference to the following detailed description of the disclosed subject matter when considered in connection with the following drawings, in which like reference numerals identify like elements.

The drawings are not necessarily to scale, or inclusive of all elements of a system, emphasis instead generally being placed upon illustrating the concepts, structures, and techniques sought to be protected herein.

Figure 1:
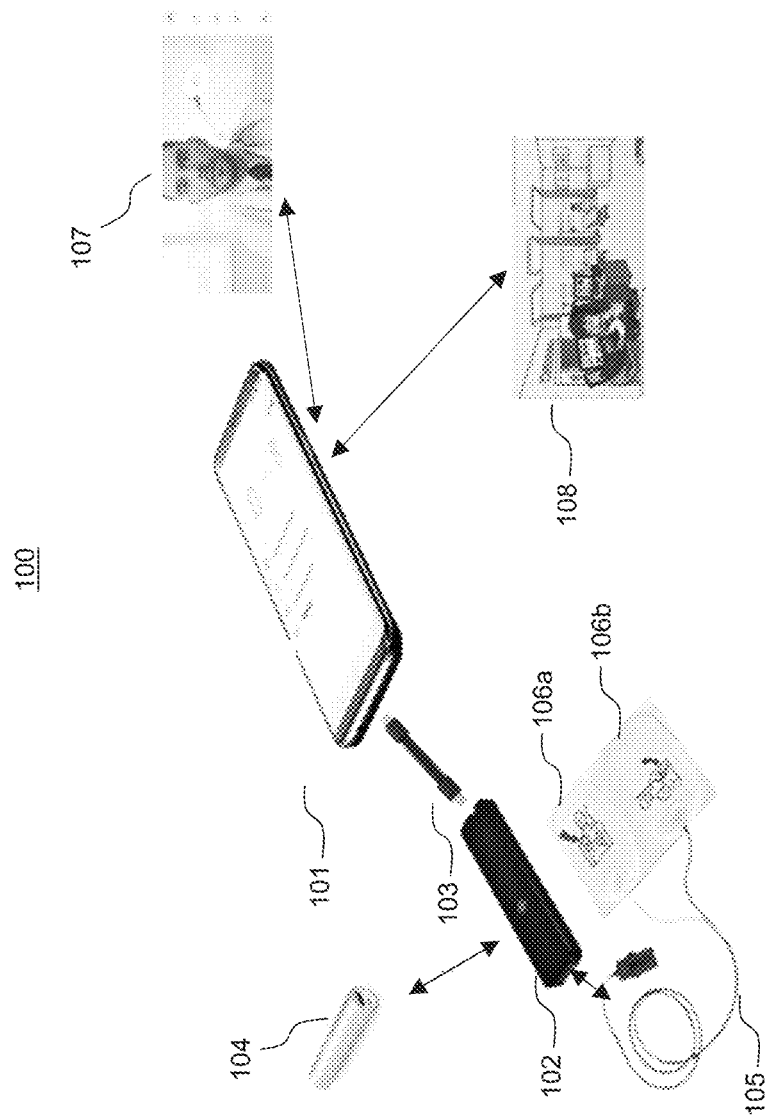
FIG. 1 is an example mobile automatic external defibrillator (AED) system according to some embodiments of the present disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

The structural components of the security system have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DESCRIPTION

The following detailed description is merely exemplary in nature and is not intended to limit the invention or the applications of its use.

The availability of public defibrillators or automated external defibrillators (AEDs) can have a significant impact on survival for people that experience cardiac arrest. Cardiac arrest victims who receive an electrical shock from a publicly available AED have much higher survival rates. For every minute without cardiopulmonary resuscitation (CPR), the chance of death can increase by ten percent.

Embodiments of the present disclosure relate to a mobile AED that can be controlled via the processing power of an external device, such as a smartphone, tablet, laptop, watch, car entertainment system, etc. The mobile AED of the present disclosure can be smaller and more widely available than any previous attempts. Any person that has access to devices that have microphones, speakers, data storage, and power sources can be used. The pads/electrodes that are used in conjunction with the mobile AED can include accelerometers and the defibrillator unit can include an electrical shock circuit. This can create a mobile AED that is easily carried around and more versatile.

In some embodiments, the mobile AED of the present disclosure can be utilized in accordance with various advantageous charging and communication techniques. For example, the disclosed mobile AED can be operable to undergo wireless charging, as well as reverse wireless charging (e.g., charging wirelessly from a mobile device). In addition, the disclosed mobile AED can include a redundant (i.e., additional) charging port that can allow for increased power-redundancy. In addition, various power selection processing techniques can be utilized to change a primary source of power of the mobile AED during operation, which can provide advantageous benefits such as preventing a mobile AED from running out of power at a critical stage of a resuscitation process.

In addition, the mobile AED of some embodiments of the present disclosure can include one or more pads/electrodes that include needles configured to pierce the skin of the subject during defibrillation, which can offer various benefits such as reduced skin resistance and better fixation between the subject and the pads. This can also reduce the energy need in the pulse, thereby reducing capacitor need/size for the AED.

In some embodiments, the mobile AED of the present disclosure can be utilized in accordance with an advantageous processing technique that can detect and read the heartbeat of the subject while the AED is being charged. This allows for an earlier shock to be delivered to the subject which can increase the likelihood of survival.

In some embodiments, the mobile AED of the present disclosure can be utilized in accordance with an advantageous charging technique that allows for faster charging of the AED. This can be referred to as a residual charging technique, utilizing the residual charge in the capacitor of the AED from a previous shock to assist in reaching the energy level for a subsequent shock.

FIG. 1 is an example mobile AED system 100, according to some embodiments of the present disclosure. Mobile AED system 100 can include a defibrillator unit 102 removably connected via connection 103 to a device 101. Defibrillator unit 102 can include circuitry configured to generate specific pulses or shocks to administer to a patient for treating cardiac arrest victims (see FIG. 2). Note, while device 101 is a smartphone in this illustration of mobile AED system 100, this is not limiting. Device 101 could be other devices with an operating system capable of running an application, such as a tablet, laptop, computer, watch, or car entertainment system. In some embodiments, connection 103 can include a USB-C connection or other similar connections. Connection 103, when connecting device 101 and defibrillator unit 102, can allow for defibrillator unit 102 to be controlled via a user interface and application on device 101. In some embodiments, defibrillator unit 102 can optionally include an additional connection port to power bank 104 (e.g. portable charger, outlet, etc.), which can also be a USB-C port, but may be different than the port for connection 103.

Defibrillator unit 102 can include an additional port for connection to a wire 105; wire 105 can act as a medium for which shocks determined and/or generated by circuitry within defibrillator 102 can be transferred to pads 106*a-b*. Pads 106*a-b* can be any standard defibrillator pads known in the art and can be configured to stick to a patient's body and operate as electrodes to feed current into a person's body from the defibrillator unit 102. In some embodiments, pads 106 can also be the pads described in relation to FIG. 5. In some embodiments, pads 106*a-b* can also include accelerometers. In some embodiments, the pads 106*a-b* can also include more intelligent sensing equipment, such as circuitry for ultrasound detection of blood flow and/or light sensors for oxygen saturation, which could be particularly helpful for self-rescue procedures. In some embodiments, when defibrillator unit 102 is connected or plugged into device 101, a user can connect to a video assistant specialist 107. In some embodiments, a team of specialists can work on call and can communicate with a user of the device. For example, if someone suddenly experiences cardiac arrest, a nearby person could connect the defibrillator unit 102 to device 101, navigate to the application (or the application can open automatically in response to connection), and select an option to immediately join a video session with a specialist, who can help the person administer a shock and/or CPR to the victim. In some embodiments, a person can also, via the application on device 101, connect to emergency services (e.g. call 911). In some embodiments, the application on the device 101 can be configured to be controlled remotely by emergency personnel or a mobile AED specialist. This can allow for, since the defibrillator unit 102 is controlled by the application on the device 101, emergency personnel to actually control and implement electrical shocks to a subject connected to the defibrillator unit 102. In some embodiments, defibrillator unit 102 can be configured to receive power from 220 V power sources or sockets or from 12 V sockets in a vehicle.

In some embodiments, the defibrillator unit 102 can be integrated into a vehicle. For example, the defibrillator unit 102 can be fully integrated, with the only visible part being long-wired pads (4 m or more), or it can be a modular defibrillator unit 102 similar to the original device that can either be connected to a mobile phone or the app on the car. This will make the defibrillator unit 102 more accessible for use in many situations.

In some embodiments, the mobile AED system 100 of FIG. 1 can be the same or similar to the devices described in U.S. Pat. Nos. 11,173,315 and 11,439,837, both of which are herein incorporated by reference in their entireties.

Figure 8:
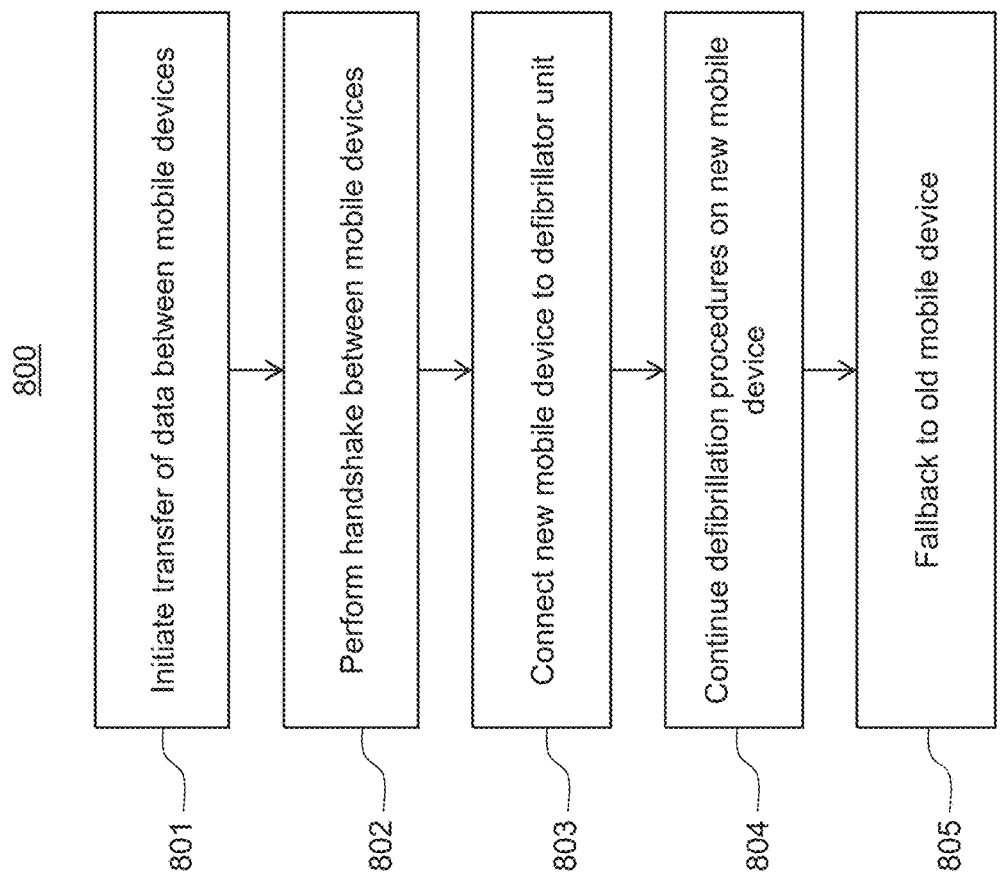
FIG. 8 is a process for charging a mobile AED according to some embodiments of the present disclosure.

In some embodiments, the defibrillator unit 102 can include a circuit design that allows for the safe preservation of charge within the capacitor, enabling the charging process described in FIG. 8. In some embodiments, the defibrillator unit 102 can include redundant charging ports, such as those consistent with the charging configurations described in relation to FIGS. 3A-3D.

In some embodiments, the application on the device 101 can also be configured to receive data from external devices connected to user device 101, such as a smartwatch or other similar device that monitors the subject. For example, a person's smartwatch may consistently monitor their heartbeat and transmit this information to user device 101. In these embodiments, the effect of defibrillation can be improved using the signals from the smartwatch in addition to the pads 106*a-b*. Application 304 can be configured to monitor and analyze the subject's heartbeat and potentially identify and/or detect dangerous rhythms (e.g., rapid ventricular tachycardia, ventricular fibrillation, or other rhythm indicators that a neural network has been trained to detect). In response to detecting a dangerous rhythm, the application can be configured to notify the subject via device 101 and instruct them to connect their mobile AED and pads and potentially begin a self-rescue protocol.

Figure 6:
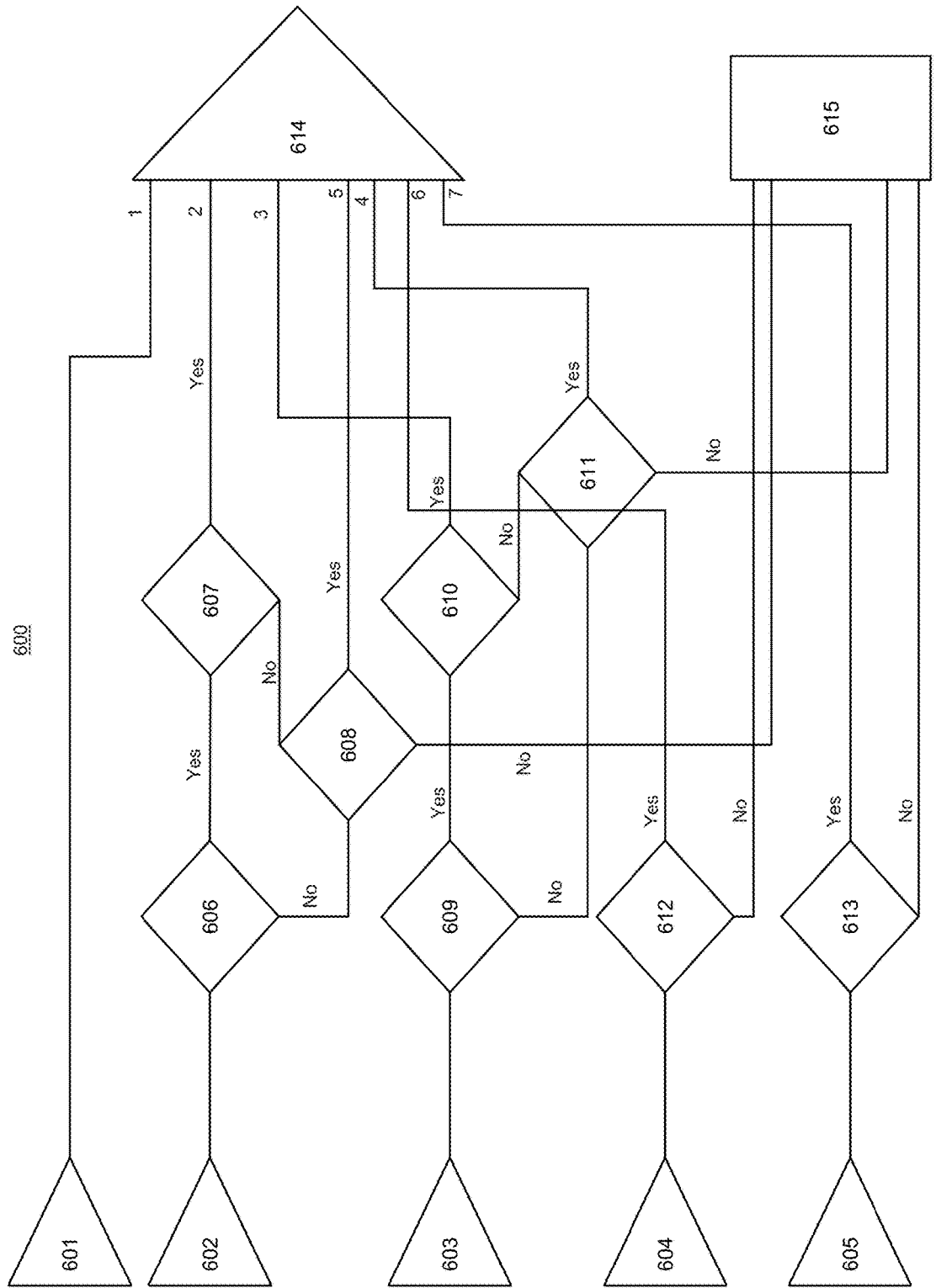
FIG. 6 is a mobile AED power source selection decision flow according to some embodiments of the present disclosure.
Figure 7:
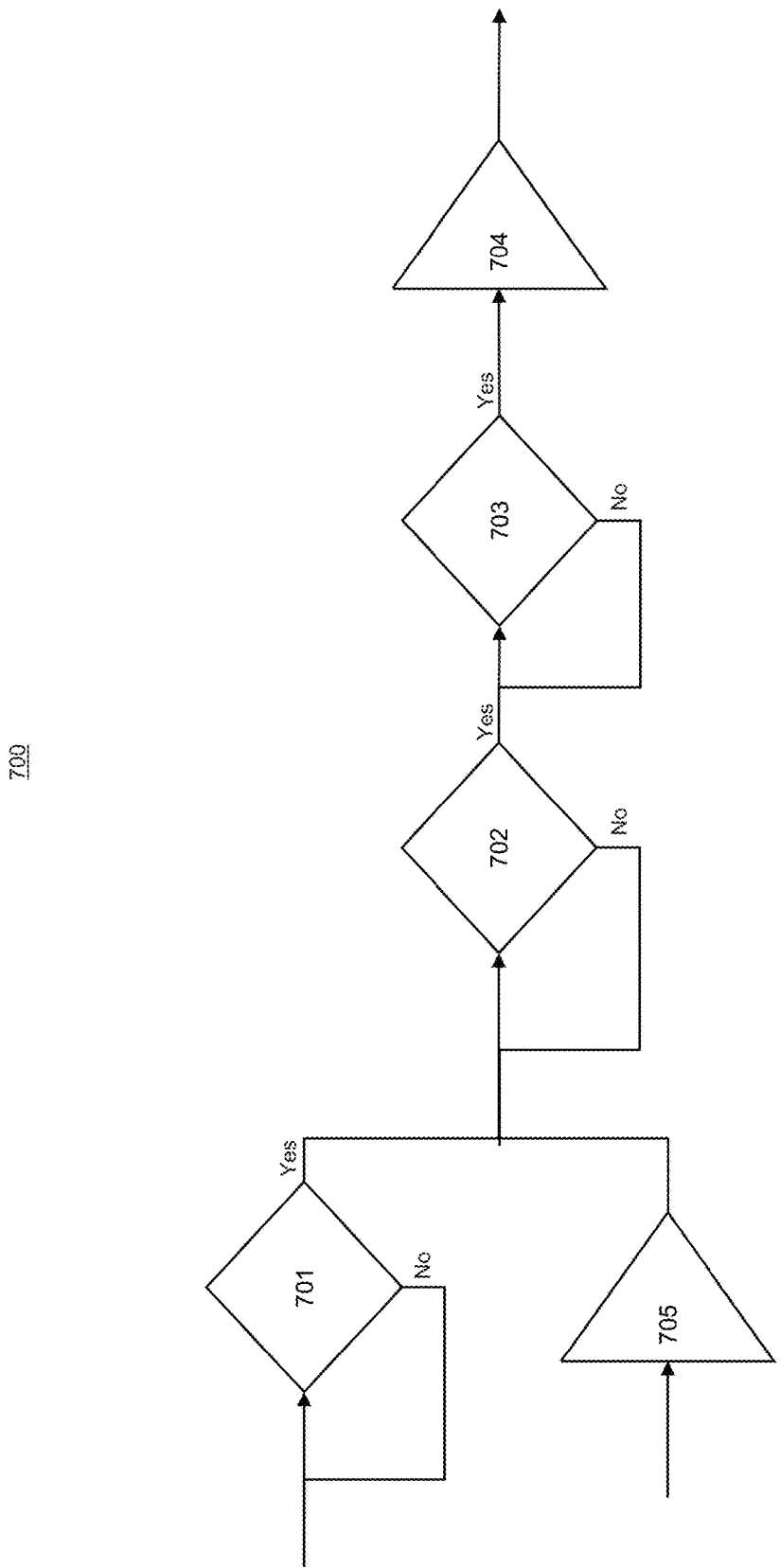
FIG. 7 is a switch mobile controller decision flow according to some embodiments of the present disclosure.

In addition, the application on the device 101 can be configured to, via one or more processors on the mobile device 101, perform the processing techniques described in relation to FIGS. 6 and 7 for selecting a power source and for performing a mobile controller switch.

Figure 2:
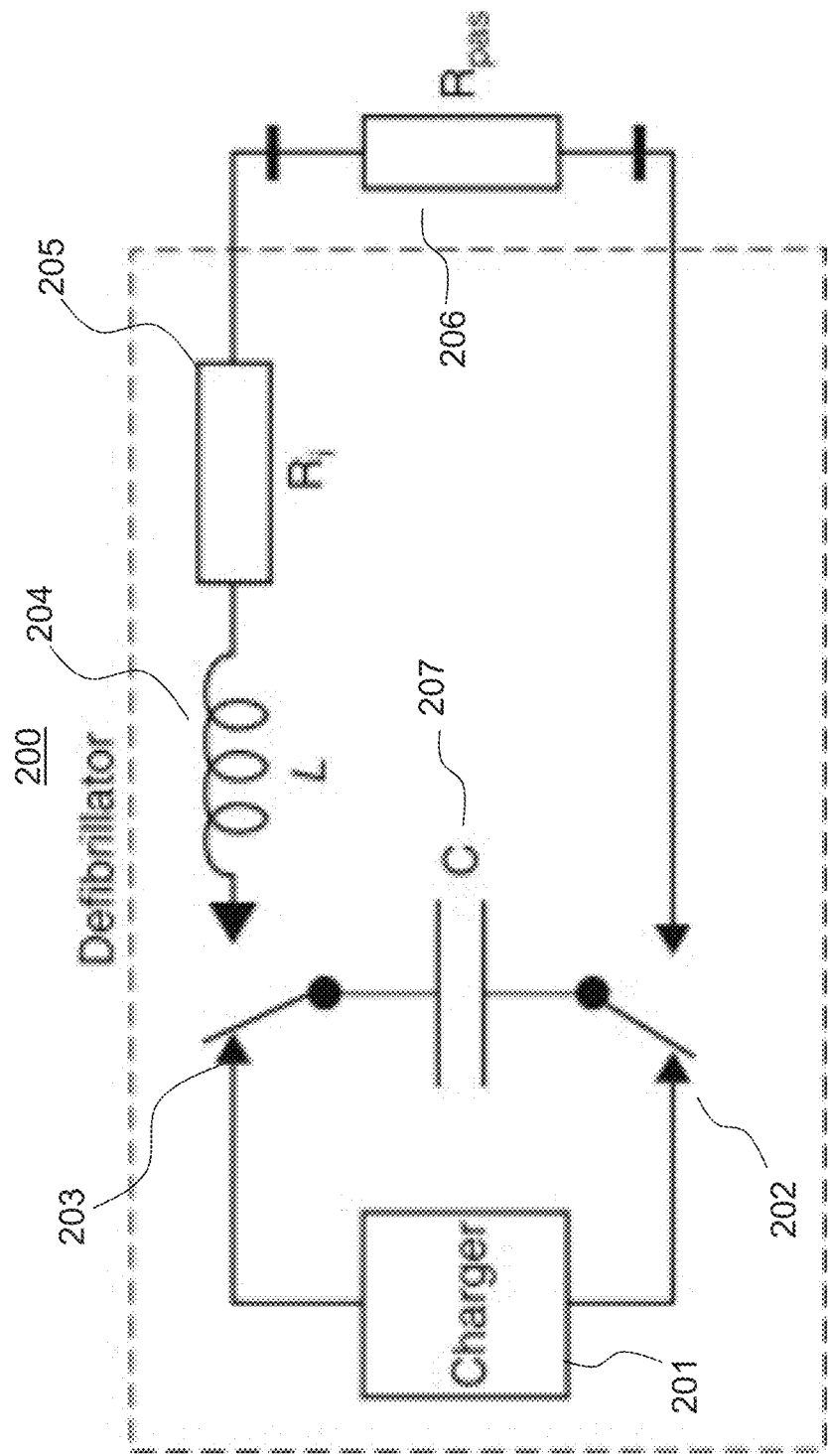
FIG. 2 is an example circuit schematic of a mobile AED according to some embodiments of the present disclosure.

FIG. 2 is an example circuit schematic 200 of a mobile AED, according to some embodiments of the present disclosure. Circuit 200 can be included within the defibrillator unit 102 of FIG. 1. In some embodiments, circuit 200 can include a charger 201, switches 202 and 203, an inductor 204, resistor 205, pass resistance 206, and capacitor 207. In some embodiments, pass resistance 206 can represent the resistance within a person's body that exists between pads 106*a* and 106*b* while they are connected. When switches 202 and 203 are in a leftward position (as shown in FIG. 2), charger 201 can charge the capacitor 207. In some embodiments, charger 201 can represent the battery of a connected device (e.g. device 101 of FIG. 1), an external power bank (e.g. power bank 104 of FIG. 1), or a combination of both. Switches 202 and 203 can be controlled via logic within device 101 and via the application that a user can navigate on the device 101. For example, the application can determine a time in which a shock (e.g. pulse of current/energy) should be administered to the patient, and, in order to administer the shock, the switches 202 and 203 move to the rightward position (not shown in FIG. 2), which can allow current to flow from capacitor 207 through the patient, inductor 204, and resistor 205. The current, when flowing through the patient's heart, can serve to resuscitate the subject until paramedics or other emergency response teams can stabilize the subject. In some embodiments, the circuit 200 can be configured to provide pulses of up to 200-360 J or more and repeatedly for up to one hour or even 90 minutes or more.

FIGS. 3A-3D show various charging configuration of a mobile AED according to some embodiments of the present disclosure. The defibrillator unit 102 can include a redundant (i.e., second) charging port. In some embodiments, the redundant charging port can be a secondary USB-C port and/or a wireless charging capability. In addition, the defibrillator unit 102 can be configured to be fully power-redundant.

Figure 3B:
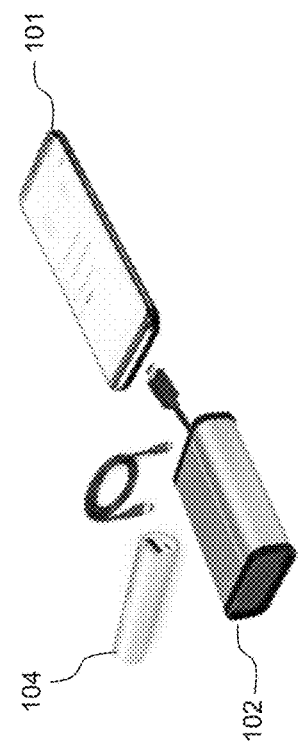
FIGS. 3A-3D show various charging configuration of a mobile AED according to some embodiments of the present disclosure.
Figure 3D:
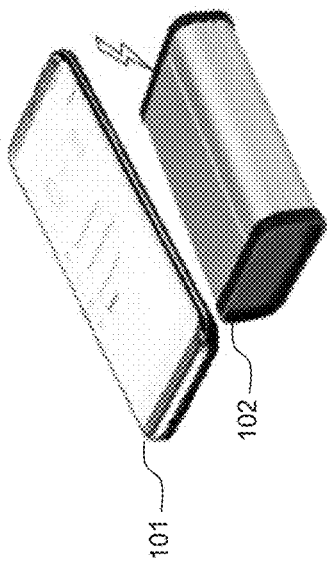
Figure 3A:
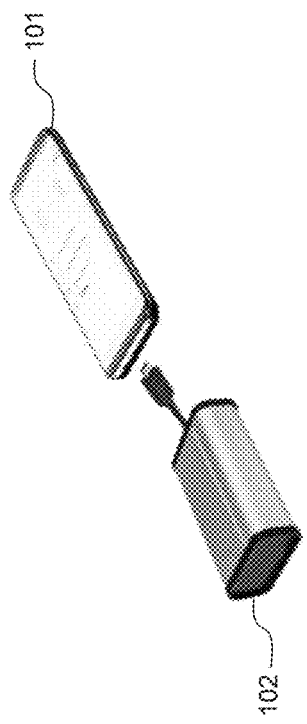
Figure 3C:
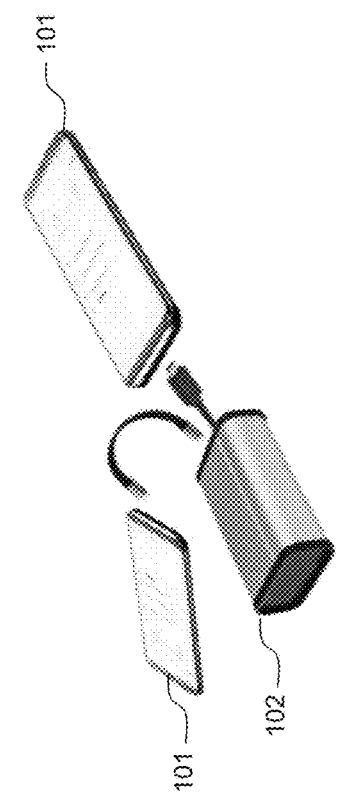

FIG. 3A shows charging of the defibrillator unit 102 receiving a charge from a mobile device 101 via a USB-C connection cable plugged into one of its charging ports. FIG. 3B shows the functionality of the defibrillator unit 102 receiving a charge from either a mobile device 101 via one charging port or via an external battery charger via the secondary charging port. FIG. 3C shows the defibrillator unit 102 receiving a charge from either a mobile device 101 via one charging port or via the second charging port from a second mobile device 101.

FIG. 3D shows the defibrillator unit 102 receiving a charge from a mobile device 101 wirelessly. In some embodiments, the defibrillator unit 102 is configured to be powered wirelessly via wireless charging that utilizes the Qi wireless standard. In some embodiments, such wireless charging can be from either a Qi charging device (not shown) or a mobile phone with reverse wireless charging. Qi is generally known as an open interface standard that performs wireless power transfer via inductive charging over distances of up to about 4 cm and is supported by many manufacturers. For example, there are currently about eighty available models of phone that support reverse wireless charging, which allows the phone to charge other devices (e.g., smartphone, smart watch, smart band, the present defibrillator unit 102).

In some embodiments, the defibrillator unit 102 can include USB-C cable charging, wireless charging, or both. Wireless charging today can support up to about 10 W for reverse wireless charging or up to 80 W or more for Qi-supported devices, although this likely will increase in the near future. In some embodiments, the defibrillator unit 102 can include redundant charging posts (e.g., a secondary USB-c or wireless charging capabilities). If the defibrillator unit 102 is at risk of running out of power (i.e., the device charging it or providing it power), a secondary power source can be connected to continue the charging and continue the defibrillation process. The power switching selection process is described in relation to FIGS. 6 and 7. In some embodiments, the power charging capabilities can also be USB3.2 or USB4.0.

Figure 4:
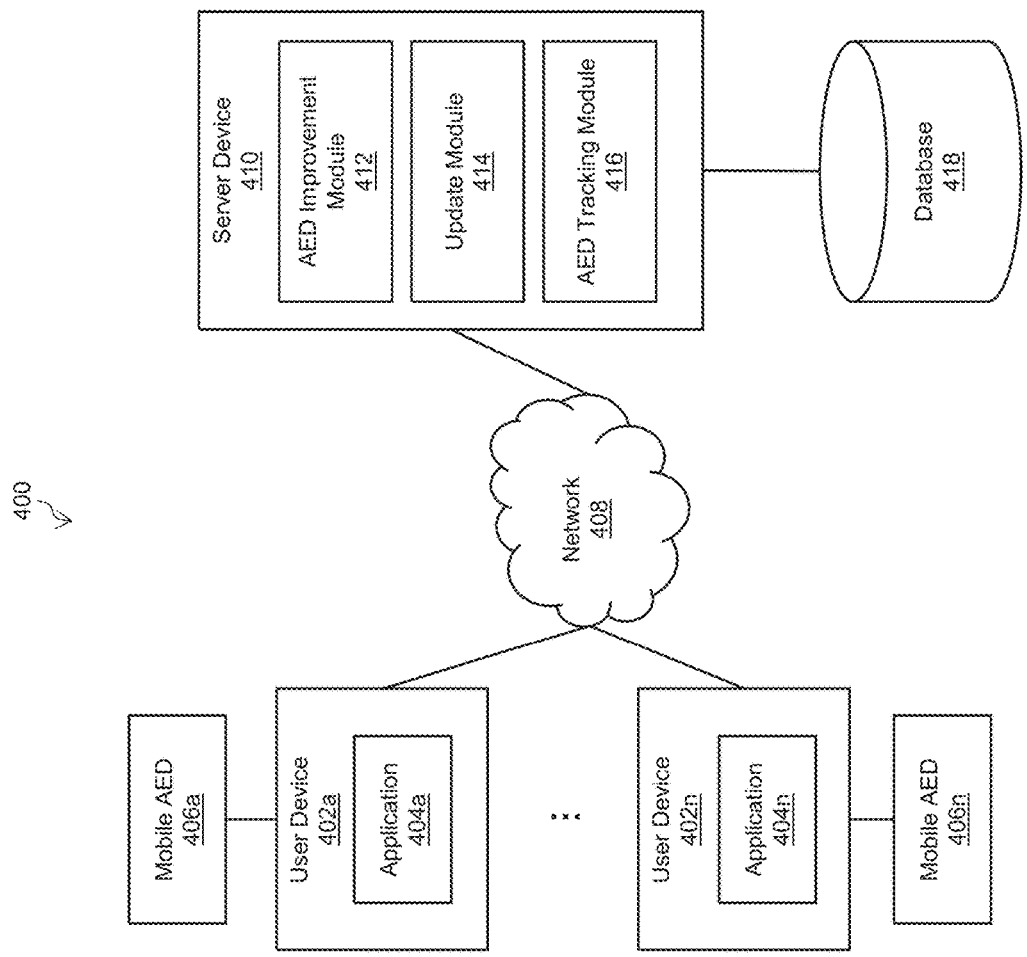
FIG. 4 is a block diagram of a system of mobile AED devices according to some embodiments of the present disclosure.

FIG. 4 is a block diagram of a system 400 of mobile AED devices according to some embodiments of the present disclosure. In some embodiments, system 400 can include a plurality of user devices 402a-n (user device 402 generally) communicably coupled to server device 410 via network 408. Note, system 400 includes two user devices 402a-n for illustrative purposes but any number of user devices can be included within the system of the present disclosure.

In some embodiments, network 408 may include one or more wide areas networks (WANs), metropolitan area networks (MANs), local area networks (LANs), personal area networks (PANs), or any combination of these networks. Network 408 may include a combination of one or more types of networks, such as Internet, intranet, Ethernet, twisted-pair, coaxial cable, fiber optic, cellular, satellite, IEEE 801.11, terrestrial, and/or other types of wired or wireless networks. Network 408 can also use standard communication technologies and/or protocols.

In some embodiments, a user device 402 can be similar to or the same as device 101 of FIG. 1. For example, user device 402 can include a smartphone, tablet, laptop, watch, car entertainment system, or a combination of similar types of devices that can run a software application and utilize an operating system. A user device 402 can include one or more computing devices capable of receiving user input as well as transmitting and/or receiving data via network 408 or communicating with server device 410. In some embodiments, user device 402 can include a conventional computer system, such as a desktop or laptop computer. Alternatively, user device 402 can include a device having computer functionality, such as a personal digital assistant (PDA) or other suitable device. Additionally, each user device 402 can include a specifically installed application 404 for use in conjunction with a connected mobile AED 406. Application 404 can include software instructions, which can be stored on a non-transitory computer readable medium, that, when executed by a processor (e.g. a processor within user device 402), can perform various processes related to administering shocks as an AED and reading EKGs in conjunction with a mobile AED 406.

In some embodiments, application 404 can include further instructions for reading a heartbeat of the patient as the defibrillator unit 406 is being charged. Instead of reading and analyzing the heartbeat, and then waiting until the device is fully charged, as conventional AED devices do, the disclosed embodiments can simultaneously implement the ability to charge the defibrillator unit 406 unit as it reads and analyzes the heartbeat. In this way an earlier shock can be applied when needed. The user device 402 will have the processing power to accomplish both tasks, and this will also be possible because there is full duplex communication (i.e., simultaneous communication in both directions) over USB-C while charging over the same cable. For example, at full duplex, a full-featured USB-C cable that implements USB 3.1 Gen. 2 can handle a data rate of up to ten Gbit/s. At the same time, there are separate lines within USB-C for charging (Vbus), so that one device can send charging power on one line within the cable while communicating both ways at full speed on other lines in the same cable. In effect, the user device 402 can receive and interpret electrical signal information from the pads (e.g., pads 106) while charging. This will both improve the resulting treatment, as a deeper, and online assisted analyze of the signal can be performed, over a longer period of time than a traditional AED.

In some embodiments, the application 404 a full, non-interrupted focus when performing a rescue procedure, which can be achieved via a deep integration with the operating system of the user device 402. For example, a user can access the app without a lock code. Because the owner of the app may be the person with the cardiac arrest, the app can start immediately and without entering the lock code if the AED device is connected. For example, the application 404 can 1) start automatically and immediately when a cable is connected or during an app synchronization switch; 2) control output of power via the USB port; 3) takeover the screen completely without being interrupted by the mobile phone OS; 4) timing-wise be able to send and receive commands to and from the AED device without being interrupted or delayed; 5) access to full duplex video and microphone/speakers; 6) access to read battery level; 7) access to GPS/NFC/BT, etc.; 8) access to emergency call function and related capabilities (i.e. notify emergency contacts); and 9) stop other apps from running, including energy intensive apps or apps using the USBV port, BT, NFC, video and loudspeaker.

Server device 410 may include any combination of one or more of web servers, mainframe computers, general-purpose computers, personal computers, or other types of computing devices. Server device 410 may represent distributed servers that are remotely located and communicate over a communications network, or over a dedicated network such as a local area network (LAN). Server device 410 may also include one or more back-end servers for carrying out one or more aspects of the present disclosure. In some embodiments, server device 108 may be the same as or similar to server device 700 described below in the context of FIG. 10.

As shown in FIG. 4, server device 410 can include an AED improvement module 412, an update module 414, and an AED tracking module 416. Additionally, server device 410 can be communicably coupled to a database 418. In some embodiments, AED improvement module 412 can include one or more models/algorithms trained via machine learning that can be used to continuously improve AED and/or CPR performance overtime. In some embodiments, AED improvement module 412 can be configured to continuously receive performance data from user devices 402 and retrain or update models to reflect newly received performance data. In some embodiments, AED improvement module 412 can also have access to Emergency Health Records and other external databases to obtain additional training data. In some embodiments, AED improvement module 412 can be configured to analyze, retrain, and/or update various machine learning models related to AED performance, such as models that determine lengths and levels of initial pulses, pad placement, body part detection, how often to provide additional pulses, the amount of energy in each pulse, and various other decisions related to electrocardiogram (EKG) readings. In some embodiments, the decisions can also be made based on other data related to the use of the mobile device interface, such as time spent on different screens, the number of times the back function is used, general timing of use, etc., to improve and optimize the user experience.

In some embodiments, update module 414 can be configured to package or incorporate updated/retrained models from AED improvement module 412 into a software update and distribute the update to the user devices 402. In some embodiments, the update may be received by user device 402 via download from an application store. In addition, AED tracking module 416 can be configured to track locations of each mobile AED 406. In some embodiments, AED tracking module 416 can utilize GPS coordinates (or any positioning signal) obtained from user device 402. In some embodiments, AED tracking module 416 can allow for a user to, via the application 404 on a user device 402, search for nearby mobile AEDs 406.

The various system components-such as modules 412-316 and 404a-n—may be implemented using hardware and/or software configured to perform and execute the processes, steps, or other functionality in conjunction therewith.

Figure 5:
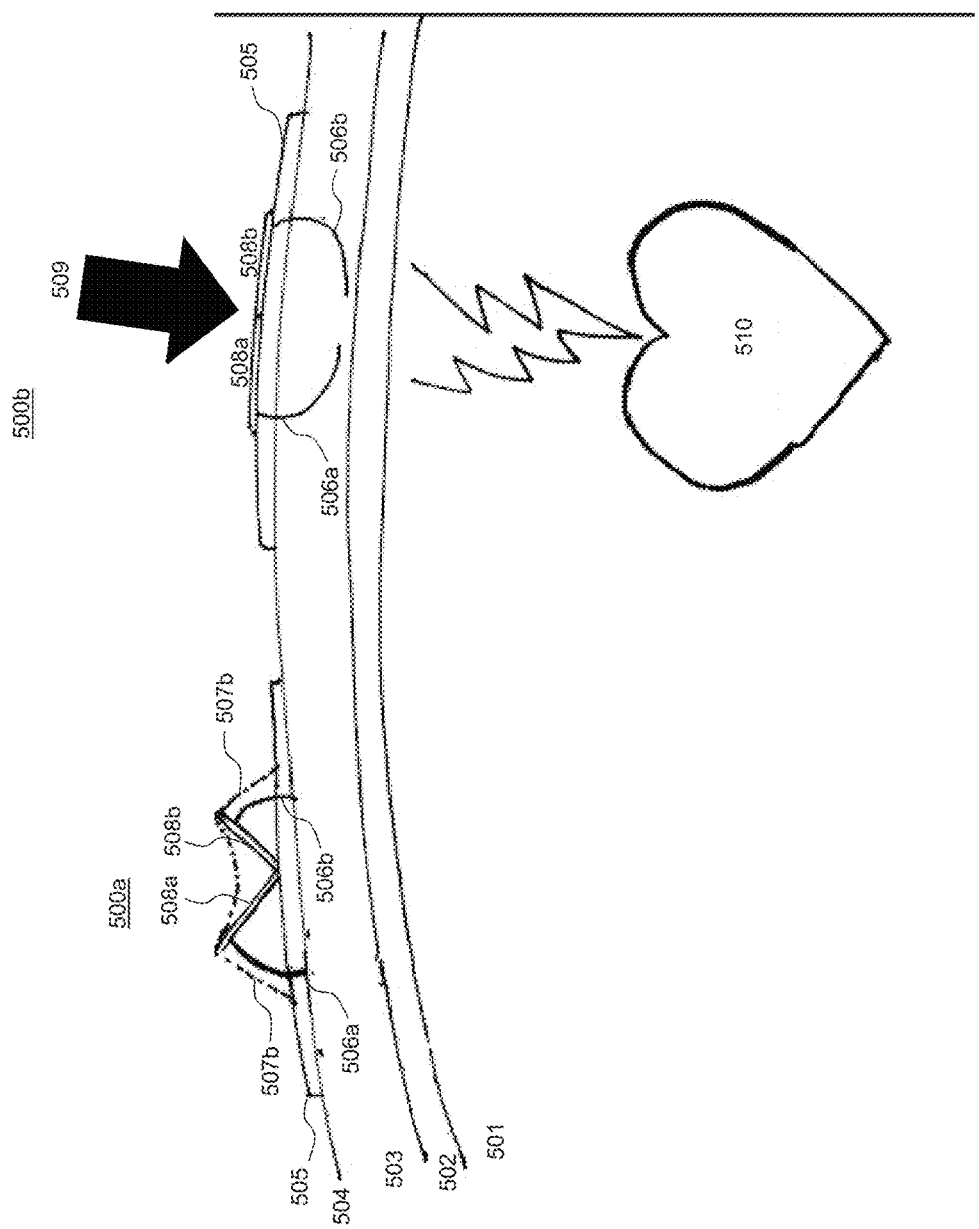
FIG. 5 shows an example pad for use with a mobile AED according to some embodiments of the present disclosure.

FIG. 5 shows an example pad for use with a mobile AED according to some embodiments of the present disclosure. The left side of FIG. 5 (500a) shows pad 505, before the pad 505 has been activated. Pad 505 includes electrodes 508a-b, fabric 507a-b, and needles 506a-b. Fabric 507 can include neoprene or another suitable dense, flexible material. The needles 506a-b can comprise a metal material, can be sharp enough to pierce the skin 504 of the subject, and can be curved to avoid puncturing lungs 501. Although pad 505 has two needles, this is not limiting and any number of needles is possible. The pad 505 rests on the skin 504 (cutis) of a subject. The additional layers of the subject include the under skin 503 (sub cutis), the ribs 502, and the lungs 501, as well as heart 510. In some embodiments, the needles 506 can be attached with a blunt end to the underside of plastic plates, which can be fixed to the pad 505 via a flexible joint, therefore constituting flaps that are ready for use in a tiled position. The pointed end of the needle is positioned inside the pad 505, near the glued side, but not penetrating. Such pads 505 may, in some embodiments, need a slightly thicker surface tissue to not be spontaneously punctured. In addition, the plastic plates can be attached to each other in a way that ensures resistance and inertia so that the needles 506 are only activated by a pressure above a certain pre-defined threshold, such as 10 kg. The needles 506 and plastic plates can be covered by fabric 507 to keep the area sterile. In this way, the needles 506 and plates may not be visible to the user, appearing as an elevation on the back of the pad when the needles 506 are not activated. In some embodiments, markings on the elevation can indicate that the pads 505 contain needles and that they can be activated and fixed by applying distinct pressure here.

The right side of FIG. 5 (500b) shows the pad 505 once it has been activated (e.g., via pushing a button on top of the pad 505 in the direction of arrow 509) and the needles 506a-b have pierced the skin and lie within the subcutaneous tissue (skin 503). When providing an electrical shock, a significant part of the energy used can be dissipated when passing through the skin. To reduce energy needs, as well as reduce the amount of burned skin, the pad 505 with hooked needles 506s-b can lead the shock current under the skin and to the heart 510 more efficiently. This can reduce energy requirements and therefore reduce the potential size of the defibrillator unit 102. The needles 506a-b can also reduce insistences of pads coming loose during resuscitation attempts. Conventional pads often come loose when the subject is damp, such as from sweat or when lying in water, which prevents the glue on the pads from sticking to their chest. Some helps may be reluctant to push needles into a patient, so the penetration can occur without being visible to the helper as the needles 506a-b are integrated into the pads 505. For example, the needles 506a-b may initially rest at a semi-vertical angle. In some embodiments, the pads 505 can be foldable. In addition, in some embodiments, the pads 505 may be foldable without the needles 506a-b.

On the back of the pad 505 are instructions for pressing hard, which will guide the needles 506a-b in the correct position. The needles 506a-b can have a curved shape which means that they bend off and do not penetrate the chest and lead to pneumothorax. Instead, they lie in the subcutaneous tissue 503, bringing the current to the heart 510 more easily and helping to keep the pads 505 fixed. The needles 506a-b could be activated if greater resistance in the tissue could be expected, for example if a high BMI is registered, or if a high impedance (i.e., an impedance above a predefined threshold) is measured between the electrodes/pads indicating a well isolated patient. After several failed shocks, or with low energy in the phone, the program may also suggest activating the needles 506a-b.

FIG. 6 is a mobile AED power source selection decision flow 600 according to some embodiments of the present disclosure. In some embodiments, the flow 600 can be performed via one or more processors on a mobile device (e.g., via application 404 of FIG. 4). Block 614 applies a hierarchy of suggested input priorities for selecting the source of power for the defibrillator unit 102. At block 601, if internal battery power is available, this is the highest priority power source. Another potential power source is at block 602, a USB-c input or similar. At block 606, it is determined whether USB power delivery is available. If yes, processing moves to block 607, where it is determined whether the power source can provide more than 8 W (although this value is exemplary in nature and any value could be used). If yes, this is determined to be the second highest priority power source at block 614. If, at block 607, it is determined that the power source 602 is not capable of providing more than 4 W, processing moves to block 608. Similarly, if no USB power delivery source is available at block 606, processing also moves to block 608. At block 608, it is determined whether the power source supports USB-3.0 or similar. If yes, this is determined to be the fifth highest priority power source at block 614. If no, is it determined that this is not an acceptable power source at block 615.

Another potential source at block 603 is a secondary USB-c or similar power source. At block 609, it is determined whether USB power delivery is available. If yes, processing moves to block 610, where it is determined whether the power source can provide more than 8 W (although this value is exemplary in nature and any value could be used). If yes, this is determined to be the third highest priority power source at block 614. If, at block 610, it is determined that the power source 602 is not capable of providing more than 4.5 W, processing moves to block 611. Similarly, if no USB power delivery source is available at block 609, processing also moves to block 611. At block 611, it is determined whether the power source supports USB-3.0 or similar. If yes, this is determined to be the fourth highest priority power source at block 614. If no, it is determined that this is not an acceptable power source at block 615.

Another potential power source at block 604 is a Qi-charger. At block 612, it is determined whether the Qi-charger power source at block 604 can provide more than, for example, 3 W. If yes, this is determined as the sixth highest priority power source at block 614. If no, it is determined that this is not an acceptable power source at block 615. Another potential power source at block 605 is a reverse mobile phone performing wireless charging. At block 613, it is determined whether the reverse wireless charging source can provide more than, for example, 4 W. If yes, this is determined as the lowest priority power source at block 614. If no, it is determined that this is not an acceptable power source at block 615. If multiple power sources are available, the highest priority source will be chosen at block 614 to power the defibrillator unit 102. In some embodiments, such a priority list is merely exemplary in nature and can vary based on certain design choices.

FIG. 7 is a switch mobile controller decision flow 700 according to some embodiments of the present disclosure. Flow 700 can be performed to allow for the changing of the power source to a new mobile device while defibrillation is in process on, for example, a cardiac arrest patient. In some embodiments, flow 700 can be performed over either the Internet, WiFi, Bluetooth, or NFC to exchange the status and history and transfer control to an application on the second mobile device. During flow 700, both mobile devices (e.g., mobile devices 101 of FIG. 1) can be plugged into the defibrillator unit 102 (via two charging ports). In some embodiments, flow 700 can also be performed with a defibrillator unit 102 that has only a single charging port, which would include unplugging the first mobile device and plugging the second mobile device in after synchronization.

Process 700 can be performed while a mobile device 101 is plugged into and powering a defibrillator unit 102. In addition, defibrillator unit 102 could also be in the process of performing defibrillation on a patient. At block 701, a decision is made on whether the battery of the mobile device 101 is low. In some embodiments, "low" can be defined as below a certain pre-defined threshold as standard mobile phones too (e.g., below 20% battery). If the battery is not at low battery, the flow resets. If the battery is low, processing proceedings to block 702. In addition, before block 702 begins, a user may be asked via an application input at block 705 to switch mobile devices.

At block 702, the mobile device 101 that is connected to the defibrillator unit 102 (e.g., via application 404), determines whether there is an additional mobile device 101 that is nearby and also has the same application installed by providing a query to the user, which would be displayed on the user interface of the mobile device 101. If such a mobile device is not nearby, processing resets to block 702. If such a mobile device is nearby, processing proceeds to block 703. At block 703, the first mobile device 101 detects if another mobile device is nearby, such as via NFC, Bluetooth, WiFi, etc. In some embodiments, every mobile device with the application can search for and alert nearby users with the app of cardiac arrest (or other emergency) situations. For example, the application receiving the alert can read, via USB, Bluetooth, or WiFi, whether a supported AED device is nearby, and signal back to the original app close to the cardiac arrest. The message can include the position (by GPS, WiFi) and a version of AED and mobile phone, as well as capacity (battery, etc.). The alert-sending app can then choose the best nearby option and confirm the need for assistance from that specific mobile. The owner of the alert-receiving app can then rush to help. The alert-sending app can follow on a map the position of the helper as he/she is approaching. This will work whether the app is on a mobile phone, in a car, or on a web page or personal computer. In a case where you just need the assistance in the situation (because of physical limitations, etc.), the alert via the app network will also assist you in getting help.

If the first mobile device 101 cannot detect another nearby mobile device, processing resets to block 703. If the first mobile device 101 can detect another nearby mobile device, processing proceeds to block 704, which begin a procedure for switching the power source of the defibrillator unit 102. Additional details on such the procedure for switching the power source are described in relation to FIG. 8.

In some embodiments, once there is a connection between the original mobile device and a new mobile device, an app will automatically be started on the second mobile phone. The app on the first phone connects to the second phone and ask for a switch of control. The app on the first phone synchronizes its data with the second phone. The synchronization is verified. The app on the second phone asks the user for confirmation for the switch. If yes, the app on the second phone message the app on the first phone it will initiate a switch. The app on the second phone queries the user to plug the USB cable into the phone (move it from the first phone). When the cable is plugged in the app on the second phone checks that the connected device is the same and in the same state as reported by the first phone. The app on the second phone now controls the procedure and the device and message is sent to the first phone about a successful takeover.

FIG. 8 is a process 800 for switching the power source of a defibrillator unit according to some embodiments of the present disclosure. At block 801, the transfer of data from the old mobile device and to the new mobile device is initiated. The transferred data can include personal data that was known prior to the procedure being initiated (e.g., age, sex, weight, language, etc.), data points collected from the start of the current emergency (e.g., heart signals, number of shocks, timings, etc.), current state information (e.g., capacitor charge level, heart state, EMS connections, etc.), and software/firmware/hardware revisions and associated digital signatures. At block 802, once the data is fully transferred, a handshake is performed between the mobile devices to validate the data. At block 803, when the data has been validated via the handshake, the new mobile phone is connected to the defibrillator unit 102. At block 804, the defibrillation procedure is continued on the new mobile device to assist the subject. At block 805, which is optional, the system may fall back o the old mobile device if any errors occur during the defibrillation procedure. This can occur via app-to-app communication.

Figure 9:
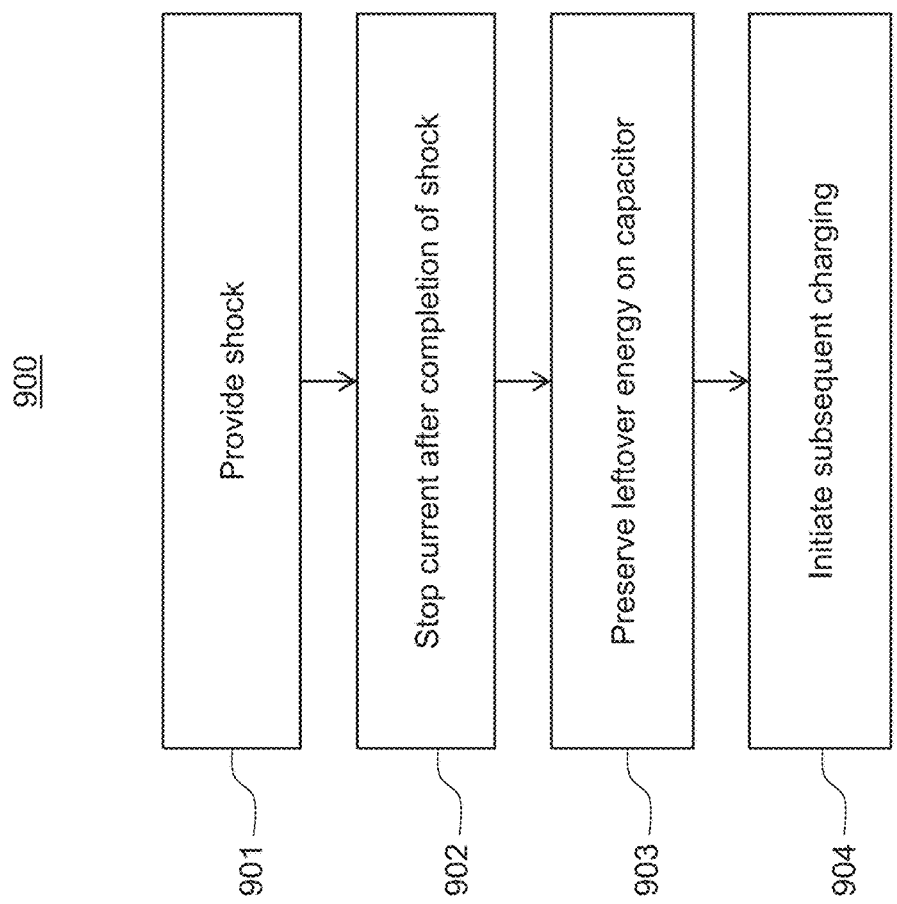
FIG. 9 is a process for charging a mobile AED according to some embodiments of the present disclosure.

FIG. 9 is a process 900 for charging a mobile AED according to some embodiments of the present disclosure. In some embodiments, process 900 is performed by the hardware in the user device 402. In some embodiments, the process 900 can be controlled by a command from the user device 402 ("Do/Do Not Drain capacitor"), or it could be controlled from the defibrillator unit itself based on safety rules (e.g., "after 3 minutes, drain capacity for safety"). Currently existing AEDs drain the capacitor after a shock as a precaution, so it is integrated in the design. For a mobile AED with significant charging time, the benefit of not draining the capacitor is important in order to be ready for the next shock. Process 900 involves saving leftover energy on the capacitor within the defibrillator unit 102 (e.g., capacitor 207) and charging on top of that in preparation for the next charge, offering the benefits of faster charging. At block 901, the defibrillator unit 102 provides a shock to a subject, such as a cardiac arrest patient. At block 902, the current is stopped after completion of the initial shock. At block 903, the energy leftover on the capacitor within the defibrillator unit is preserved. For example, after current is stopped at block 902, the capacitor is not discharged quickly as it usually is. At block 904, whenever a subsequent shock is going to be administered to a subject, subsequent charging is initiated, starting from the already charged capacitor level.

Figure 10:
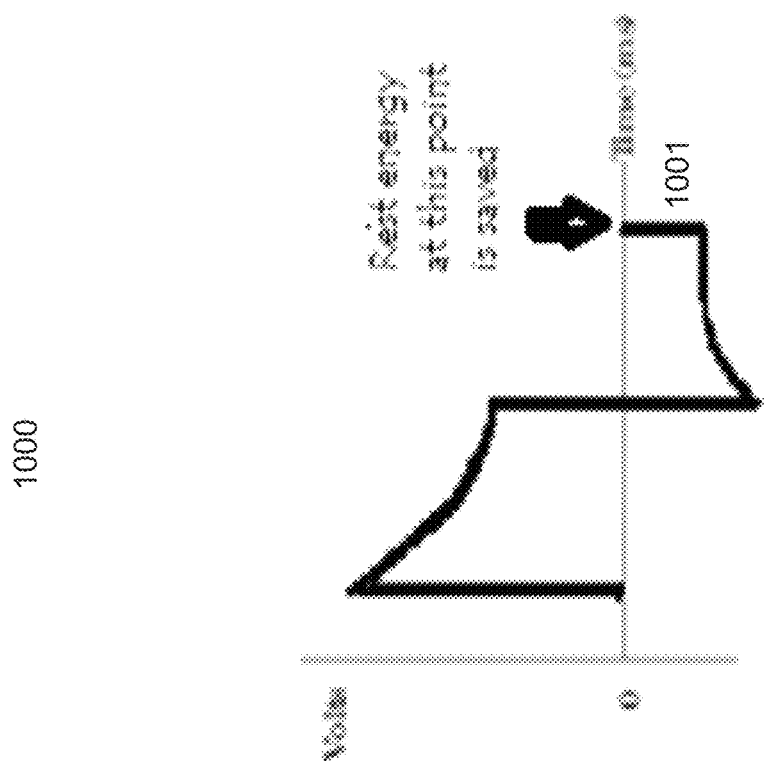
FIG. 10 shows the voltage (y-axis) as a function of time (x-axis) at the electrodes/pads according to some embodiments of the present disclosure.

FIG. 10 shows the voltage (y-axis) as a function of time (x-axis) at the electrodes/pads, such as pads 505. The voltage is similar to the voltage at the output of the capacitor 207, but after a phase switching capacitor. At the point in time where the arrow points, the safety discharge circuit typically would kick in and discharge the rest of the energy to the environment. However, the disclosed embodiments are configured to keep the rest of the charge in the defibrillator unit stored in the capacitor, decreasing charging time and the size of the device.

Figure 11:
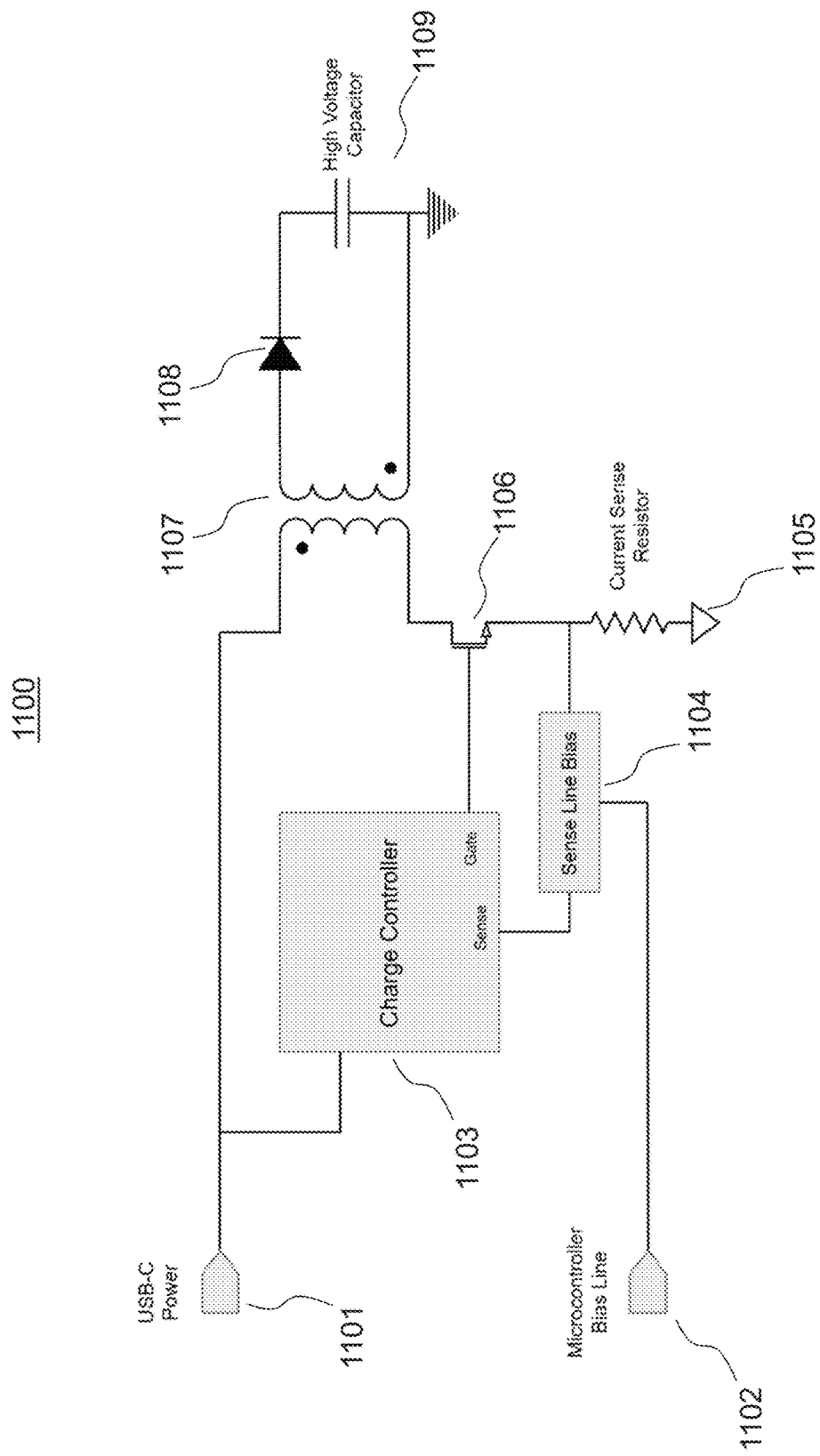
FIG. 11 shows an example circuit architecture according to some embodiments of the present disclosure.

FIG. 11 shows an example circuit architecture 1100 according to some embodiments of the present disclosure. In some embodiments, the circuit architecture 1100 can be a flyback converter charge circuit with a current sense bias circuit that can decrease charge time. Typical flyback converter circuits can be composed of a flyback transformer that is fed by a DC voltage source and switched on and off to generate a high DC voltage output. The principles disclosed herein employ the circuit architecture 1100 to charge a high voltage capacitor 1109, such as to 1900 V. Charging can be accomplished with a charge controller 1103 that switches a MOSFET switch 1106 on and off, where the switch 1106 is connected between the transformer 1107 and ground reference. When the switch 1106 is on, current flows through the transformer 1107's primary winding, and current increases linearly with time as a function of the transformer 1107's primary winding inductance. Current flowing through the transformer 1107 and switch 1103 is monitored by a current sense resistor 1105. Once the voltage across the current sense resistor 1105 increases above a threshold (e.g., 78 mV), the charge controller 1103 shuts off the switch 1106, and the energy stored in the transformer 1107 is forced in the secondary side circuit, to a diode 1108, and into the capacitor 1109. The switch 1106 is turned back on, and charging continues.

In the presently described embodiments, the current sense resistor 1105 is configured so that the switch 1106 turns off when a predefined amount of current (e.g., 2 A) flows through the transformer 1107. This corresponds to an average current draw of 0.9 A from the USB-C power source 1101. However, due to non-ideal parasitic capacitances in the flyback transformer 1107, as the high voltage capacitor 1109 increases in voltage, some of the energy from the USB-C power source 1101 gets stored in the transformer 1107 and then fed back into the USB-C power source 1101. This stored energy can be proportional to the voltage on the high voltage capacitor 1109. Potential issues that could arise can include 1) as the capacitor 1109 charges, the average current draw from the USB-C power source 1101 decreases down to 0.6-0.7 A; and 2) charge time increases due to charging efficiency decreasing as capacitor voltage increases.

The disclosed embodiments address these issues of decreased current draw by increasing the transformer 1107 current limit above 2 A and making it adjustable as capacitor 1109 voltage increased. This was accomplished by biasing the voltage across the current sense resistor 1105 with a sense line bias circuit 1104. Effectively, the bias circuit 1104 allowed for higher current to flow above 2 A before the voltage across the current sense resistor 1105 reached 78 mV. Additionally, the bias circuit 1104 was controlled with a pulse width-modulated waveform from a microcontroller 1102, where the pulse width is tuned in software. This allows for tuning of the bias circuit 1104 on the fly while the capacitor 1109 was charging. Ultimately, it allows for maximizing the current draw from the USB-C power supply 1101 during the entire charging period, and more importantly, decreasing charging time.

Figure 12:
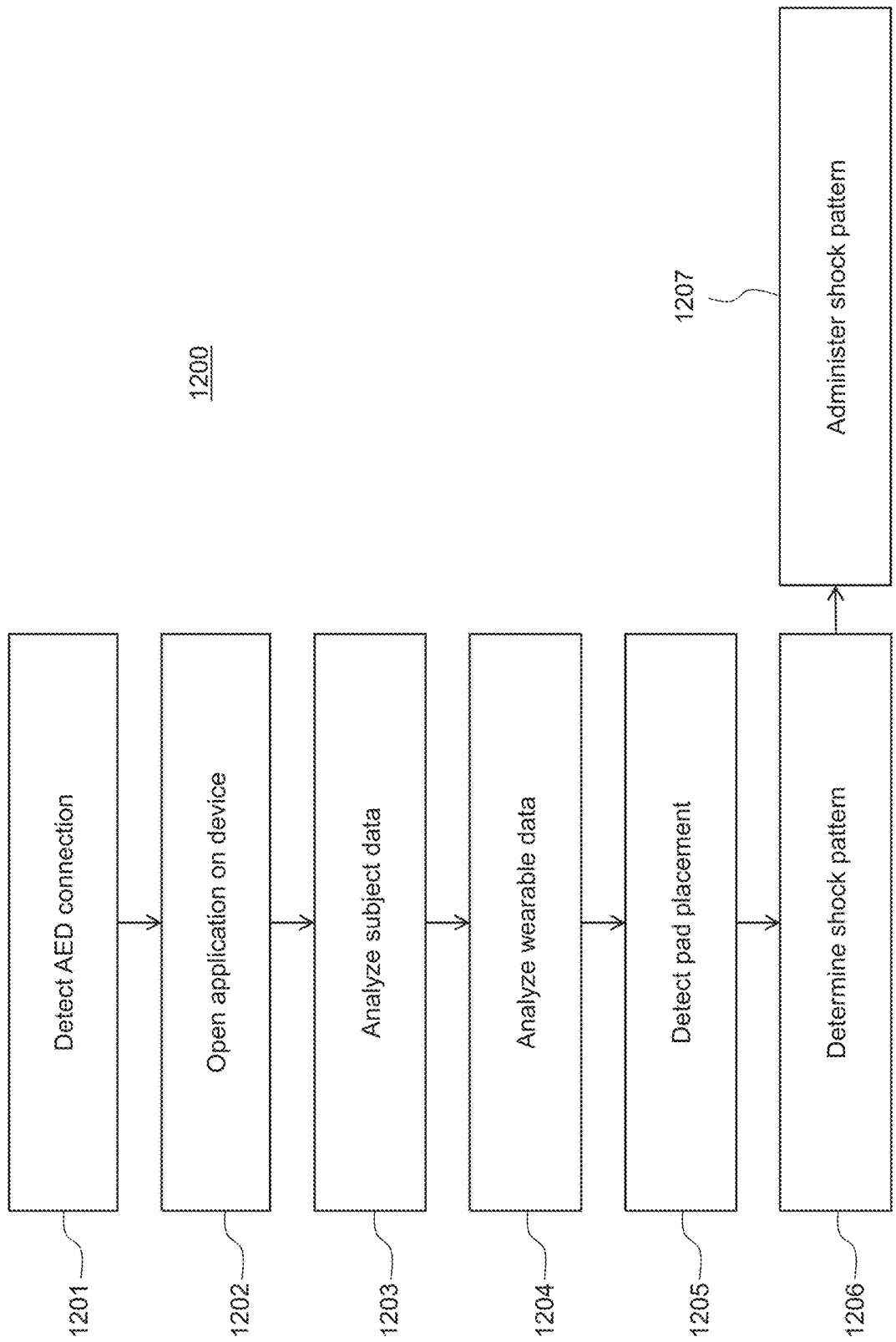
FIG. 12 is an example process for using a mobile AED according to some embodiments of the present disclosure.

FIG. 12 is an example process 1200 for using a mobile AED according to some embodiments of the present disclosure. In some embodiments, process 1200 can be performed by a user device (e.g., user device 402 and/or user device 101). In some embodiments, performance of process 1200 can be assisted by a user interacting with the user device. For example, in response to a person experiencing sudden cardiac arrest, a bystander or friend or other individual may utilize a mobile AED of the present disclosure and an application (e.g., application 404) on a user device to perform process 1200. At block 1201, user device 402 (e.g., via application 404) can detect an AED connection. For example, the user can locate a mobile AED (e.g., defibrillator unit 102) and connect the defibrillator unit 102 to the user device, such as by plugging in a connection cable. The user device, for example via application 404, can detect that the defibrillator unit 102 has been connected. At block 1202, user device 402 can open an application 404. In some embodiments, the application 404 can be automatically opened in response to detection of the defibrillator connection; in some embodiments, the application may be opened manually by the user.

At block 1203, the application 404 can analyze data associated with the subject (e.g., the person who has recently gone into cardiac arrest). For example, the application 404 may store demographic and health information associated with the subject by previously allowing the subject access to input self-describing information. The application 404 can store various types of information such as height, weight, age, blood pressure, previous EKG ratings, medical history, etc. In some embodiments, application 404 can be configured to utilize a machine learning algorithm to analyze the subject information to make various determinations related to the remaining steps for administering AED treatment. In some embodiments, the analysis can be performed external from the user device 402; for example, the subject data may be sent and processed by a server (e.g., server 410), and the results of the processing may be transmitted to the user device 402 to affect treatment.

At block 1204, application 404 can analyze wearable data, such as various biometric data obtained from a wearable device worn by the subject. This can include a smartwatch or other wearable devices. The wearable data can include a variety of data such as, but not limited to, heartrate, blood oxygen saturation levels, and others.

At block 1205, application 404 can detect a pad placement. In some embodiments, the application 404 can be configured to, based on electrical measurements (e.g., current) from the pads 106*a-b*, detect whether a human body is connected between the two pads. In some embodiments, detecting the pad placement can include, once the pads (e.g., pads 106a-b) are placed on a subject's body (e.g., under the subject's right collarbone and below the subject's left armpit), application 404 can detect the amount of current flowing through the subject and between the pads. Based on the strength of the detected current, application 404 can determine whether the pads are too far apart or too close together. For example, application 404 can utilize a threshold current range and compare the detected current to the threshold. If the detected current is above or below the threshold, application 404 can display a warning on the device to the user that recommends moving the pads closer or farther away from each other.

At block 1206, application 404 can be configured to determine a shock pattern to administer to the subject. In some embodiments, determining the shock pattern can include application 404 utilizing a machine learning model to analyze data associated with the subject (e.g., height, weight, pad placement, EKG measurements, etc.) and the wearable data and output a shock pattern to resuscitate the subject. In some embodiments, application 404 can obtain and analyze data (e.g., operate as an EKG machine) via the connected pads prior to determining a shock pattern and use the obtained data to determine the shock pattern. For example, the machine learning model can be trained to determine the shock pattern based on data such as pulse rate (both frequency and variations), all types of heart rhythm, the configuration of the EKG-complexes, ST elevations (e.g., the vertical distance inside the EKG trace and the baseline), deprivations, and signs of cardiac ischemia, ventricular tachycardia, and ventricular fibrillation. Application 404 can also be configured to detect that certain breathing patterns occurring in association with ventricular extrasystoles can be a trigger event. In some embodiments, the machine learning model can include a neural network with a plurality of nodes trained to map the aforementioned types of health data to various factors in shock patterns (e.g., durations, timing, and energy levels). In some embodiments, application 404 can be configured to estimate a subject's fat percentage based on electrical measurements received from the pads 106a-b, and the fat percentage can be used in determining the electrical shock pattern. In some embodiments, the machine learning model can also be configured to predict if subjects will get "return of spontaneous circulation" (ROCS), which can include the resumption of sustained perfusing cardiac activity. This can be predicted by analyzing breathing, movement, pulse, and blood pressure.

In some embodiments, the shock pattern can include a duration and level (e.g., energy level in Joules) of a plurality of energy pulses. In some embodiments, the initial pulse to a subject experiencing cardiac arrest can be important with regard to resuscitation. At block 1206, application 404 can cause defibrillator unit 102 to administer the determined shock pattern to the subject. Administering the shock pattern can include utilizing the power source of user device 402 to power the circuitry (e.g., circuit 200) within the defibrillator unit 102. A possible benefit of utilizing the power circuitry within a mobile device is that it can provide for a cheaper device, which can ultimately be more accessible for more people and increase the prevalence of its use. In some embodiments, application 404 can be configured to give a warning to people nearby before the electrical shock pattern is administered. For example, application 404 can utilize speakers and the user interface of the device 101 to sound off and display a warning to move away from the person while the electrical shock is being administered. This can prevent current from shocking or harming other people. In some embodiments, after the electrical shock pattern has completed, application 404 can display and sound another message indicating an all-clear.

In some embodiments, prior to determining the shock pattern at block 1207, the mobile AED can be configured to operate as an EKG for a period of time. The application can be configured to receive the data and EKG measurements and make various determinations related to the shock pattern based on these measurements. In some embodiments, upon completion of any shock pattern administered, all data/information associated with the process can be sent from user device 402 to server 410, specifically to AED improvement module 312. AED improvement module 412 can utilize the received information to update and/or retrain any machine learning models related to determining shock patterns and pad placement based on both demographic and health data and EKG measurements. In some embodiments, a large plurality of mobile AEDs could be utilized, thus providing large and rich datasets for which to continuously update algorithms and models related to the AED performance. Because of the nature of operation of the present disclosure (utilizing an application interface in a standard operating system to administer an AED), this can allow for AED performance to be continuously updated and improved upon.

In some embodiments, process 1200 can be performed in accordance with a video assistant and/or voice assistant. For example, application 404 can be configured to utilize any voice assistant functionality on the device (e.g., Alexa, Google Assistant, Siri, voice systems in vehicles, etc.). For example, if a person opens the app but does not know how to administer the AED to a victim, the person could communicate with the application 404 via voice assistant and ask for help. In some embodiments, the application can connect to a specialist via video and can activate a camera on the mobile device 402. In some embodiments, a team of specialists can be assembled that can handle the inflow of video connections. Each specialist can be equipped with the knowledge of how to operate a mobile AED 406 which can provide quick and effective assistance in the case of an emergency, as well as reliable information. This can be more beneficial than the ability to connect to a doctor or similar figure as there is no issue of availability. In some embodiments, the application 404 can also allow a user to connect immediately to law enforcement and/or emergency personnel. In some embodiments, in response to notifying law enforcement or emergency personnel through the application 404, GPS and medical data associated with the subject can be immediately forwarded to law enforcement via the application 404. This can provide valuable information to emergency personnel beforehand which can save potentially precious time once the personnel have arrived on scene.

In some embodiments, the application 404 can also assist with performing CPR in accordance with administering a shock pattern. In some embodiments, the application 404 can be configured to detect the strength of pushing that an individual is providing to a subject's chest cavity by analyzing the forces on the pads 106a-b. The application 404 can provide indications to the user such as "push harder" or "push softer."

Figure 13:
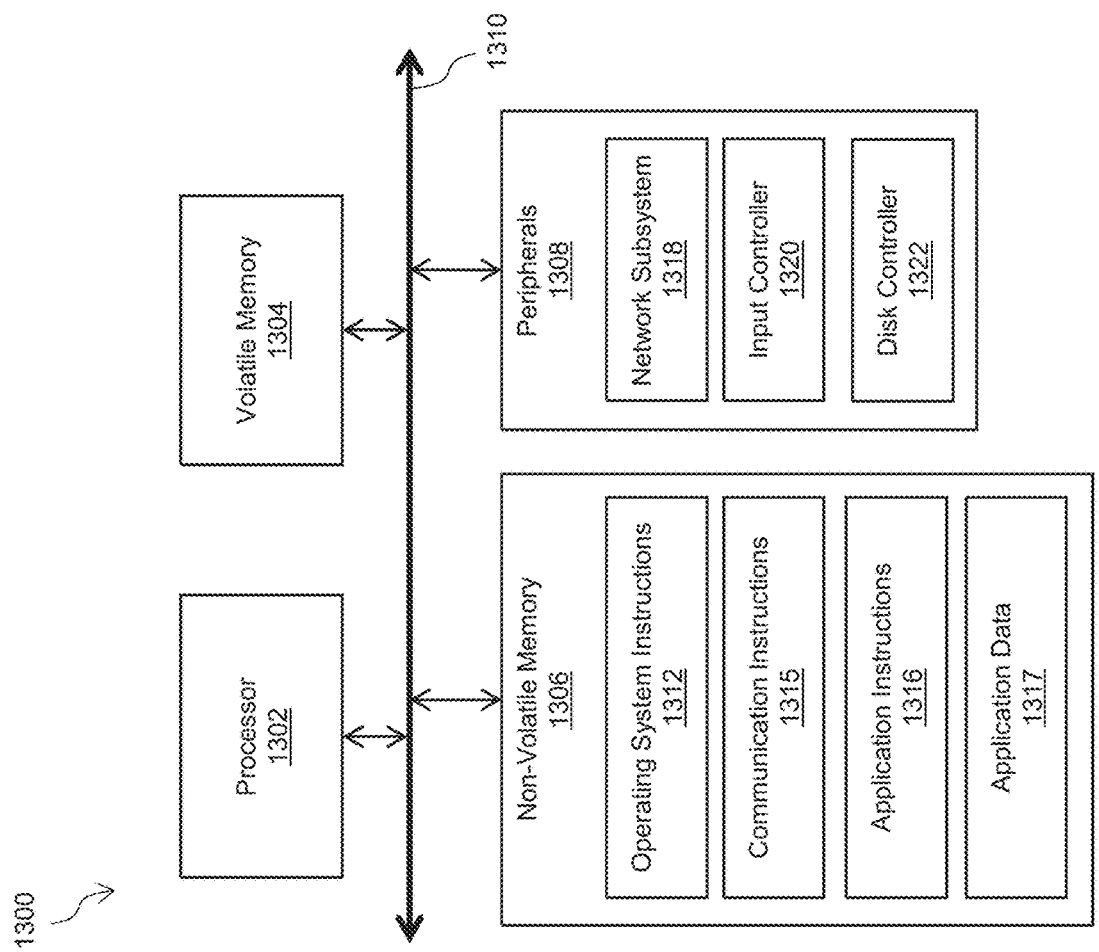
FIG. 13 is an example server device that can be used within the system of FIG. 4, according to some embodiments of the present disclosure.

FIG. 13 is an example server device 1300 that can be used within the system of FIG. 4, according to some embodiments of the present disclosure. Server device 1300 may implement various features and processes as described herein. Server device 1300 may be implemented on any electronic device that runs software applications derived from complied instructions, including without limitation personal computers, servers, smart phones, media players, electronic tablets, game consoles, email devices, etc. In some implementations, server device 1300 may include one or more processors 1302, volatile memory 1304, non-volatile memory 1306, and one or more peripherals 1308. These components may be interconnected by one or more computer buses 1310.

Processor(s) 1302 may use any known processor technology, including but not limited to graphics processors and multi-core processors. Suitable processors for the execution of a program of instructions may include, by way of example, both general and special purpose microprocessors, and the sole processor or one of multiple processors or cores, of any kind of computer. Bus 1310 may be any known internal or external bus technology, including but not limited to ISA, EISA, PCI, PCI Express, NuBus, USB, Serial ATA, or FireWire. Volatile memory 1304 may include, for example, SDRAM. Processor 1302 may receive instructions and data from a read-only memory or a random access memory or both. Essential elements of a computer may include a processor for executing instructions and one or more memories for storing instructions and data.

Non-volatile memory 1306 may include by way of example semiconductor memory devices, such as EPROM, EEPROM, and flash memory devices; magnetic disks such as internal hard disks and removable disks; magneto-optical disks; and CD-ROM and DVD-ROM disks. Non-volatile memory 1306 may store various computer instructions including operating system instructions 1312, communication instructions 1315, application instructions 1316, and application data 1317. Operating system instructions 1312 may include instructions for implementing an operating system (e.g., Mac OS®, Windows®, or Linux). The operating system may be multi-user, multiprocessing, multitasking, multithreading, real-time, and the like. Communication instructions 1315 may include network communications instructions, for example, software for implementing communication protocols, such as TCP/IP, HTTP, Ethernet, telephony, etc. Application instructions 1316 may include instructions for administering shock patterns using a mobile AED, connecting to law enforcement, displaying instructions for administering shock patterns using the mobile AED, and performing a self-rescue operation according to the systems and methods disclosed herein. For example, application instructions 1316 may include instructions for components 110-112 described above in conjunction with FIG. 1.

Peripherals 1308 may be included within server device 1300 or operatively coupled to communicate with server device 1300. Peripherals 1308 may include, for example, network subsystem 1318, input controller 1320, and disk controller 1322. Network subsystem 1318 may include, for example, an Ethernet of WiFi adapter. Input controller 1320 may be any known input device technology, including but not limited to a keyboard (including a virtual keyboard), mouse, track ball, and touch-sensitive pad or display. Disk controller 1322 may include one or more mass storage devices for storing data files; such devices include magnetic disks, such as internal hard disks and removable disks; magneto-optical disks; and optical disks.

Figure 14:
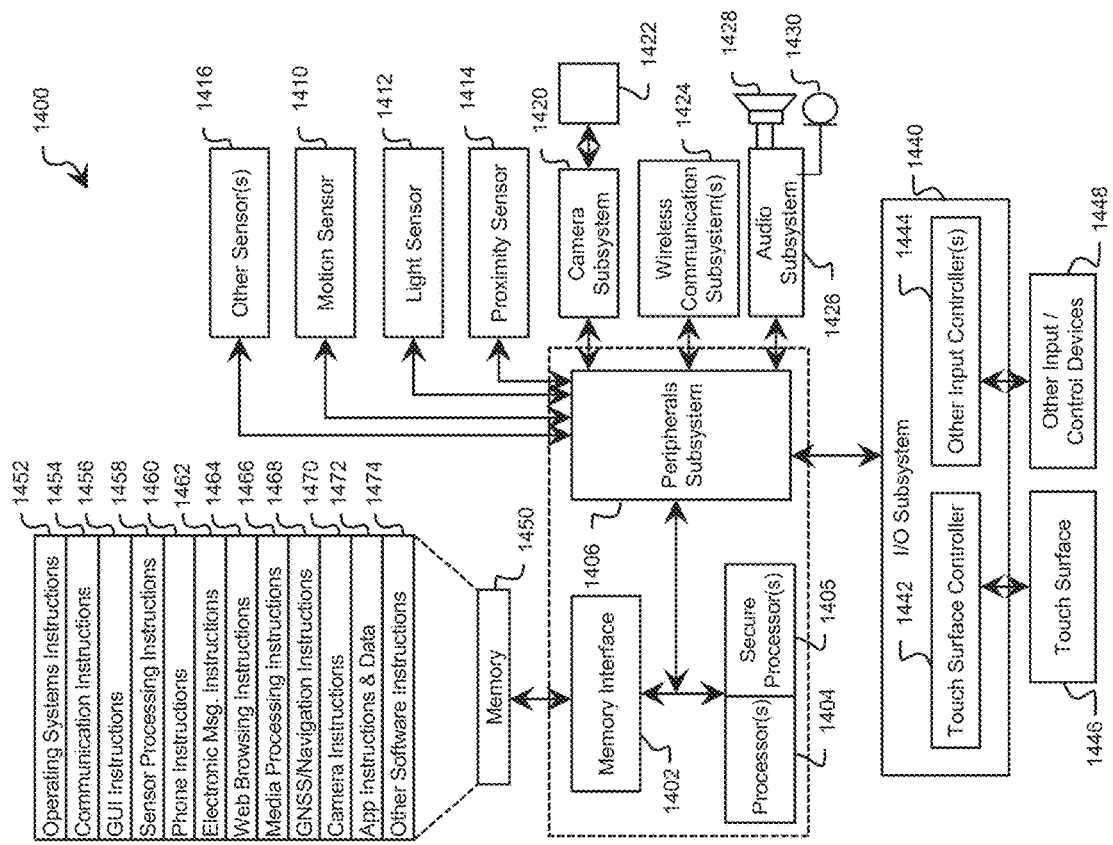
FIG. 14 is an example computing device that can be used within the system of FIGS. 1 and/or 3, according to some embodiments of the present disclosure.

FIG. 14 is an example computing device 1400 that can be used within the system of FIGS. 1 and/or 3, according to some embodiments of the present disclosure. In some embodiments, device 1400 may be user device 101. The illustrative user device 1400 may include a memory interface 1402, one or more data processors, image processors, central processing units 1404, and/or secure processing units 1405, and peripherals subsystem 1406. Memory interface 1402, one or more processors 1404 and/or secure processors 1405, and/or peripherals subsystem 1406 may be separate components or may be integrated in one or more integrated circuits. The various components in user device 1400 may be coupled by one or more communication buses or signal lines.

Sensors, devices, and subsystems may be coupled to peripherals subsystem 1406 to facilitate multiple functionalities. For example, motion sensor 1410, light sensor 1412, and proximity sensor 1414 may be coupled to peripherals subsystem 1406 to facilitate orientation, lighting, and proximity functions. Other sensors 1416 may also be connected to peripherals subsystem 1406, such as a global navigation satellite system (GNSS) (e.g., GPS receiver), a temperature sensor, a biometric sensor, magnetometer, or other sensing device, to facilitate related functionalities.

Camera subsystem 1420 and optical sensor 1422, e.g., a charged coupled device (CCD) or a complementary metal-oxide semiconductor (CMOS) optical sensor, may be utilized to facilitate camera functions, such as recording photographs and video clips. Camera subsystem 1420 and optical sensor 1422 may be used to collect images of a user to be used during authentication of a user, e.g., by performing facial recognition analysis.

Communication functions may be facilitated through one or more wired and/or wireless communication subsystems 1424, which may include radio frequency receivers and transmitters and/or optical (e.g., infrared) receivers and transmitters. For example, the Bluetooth (e.g., Bluetooth low energy (BTLE)) and/or WiFi communications described herein may be handled by wireless communication subsystems 1424. The specific design and implementation of communication subsystems 1424 may depend on the communication network(s) over which the user device 1400 is intended to operate. For example, user device 1400 may include communication subsystems 1424 designed to operate over a GSM network, a GPRS network, an EDGE network, a WiFi or WiMax network, and a Bluetooth™ network. For example, wireless communication subsystems 1424 may include hosting protocols such that device 1400 may be configured as a base station for other wireless devices and/or to provide a WiFi service.

Audio subsystem 1426 may be coupled to speaker 1428 and microphone 1430 to facilitate voice-enabled functions, such as speaker recognition, voice replication, digital recording, and telephony functions. Audio subsystem 1426 may be configured to facilitate processing voice commands, voice-printing, and voice authentication, for example.

I/O subsystem 1440 may include a touch-surface controller 1442 and/or other input controller(s) 1444. Touch-surface controller 1442 may be coupled to a touch surface 1446. Touch-surface 1446 and touch-surface controller 1442 may, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with touch surface 1446.

The other input controller(s) 1444 may be coupled to other input/control devices 1448, such as one or more buttons, rocker switches, thumb-wheel, infrared port, USB port, and/or a pointer device such as a stylus. The one or more buttons (not shown) may include an up/down button for volume control of speaker 1428 and/or microphone 1430.

In some implementations, a pressing of the button for a first duration may disengage a lock of touch-surface 1446; and a pressing of the button for a second duration that is longer than the first duration may turn power to user device 1400 on or off. Pressing the button for a third duration may activate a voice control, or voice command, module that enables the user to speak commands into microphone 1430 to cause the device to execute the spoken command. The user may customize a functionality of one or more of the buttons. Touch-surface 1446 may, for example, also be used to implement virtual or soft buttons and/or a keyboard.

In some implementations, user device 1400 may present recorded audio and/or video files, such as MP3, AAC, and MPEG files. In some implementations, user device 1400 may include the functionality of an MP3 player, such as an iPod™. User device 1400 may, therefore, include a 36-pin connector and/or 8-pin connector that is compatible with the iPod. Other input/output and control devices may also be used.

Memory interface 1402 may be coupled to memory 1450. Memory 1450 may include high-speed random access memory and/or non-volatile memory, such as one or more magnetic disk storage devices, one or more optical storage devices, and/or flash memory (e.g., NAND, NOR). Memory 1450 may store an operating system 1452, such as Darwin, RTXC, LINUX, UNIX, OS X, Windows, or an embedded operating system such as VxWorks.

Operating system 1452 may include instructions for handling basic system services and for performing hardware dependent tasks. In some implementations, operating system 1452 may be a kernel (e.g., UNIX kernel). In some implementations, operating system 1452 may include instructions for performing voice authentication.

Memory 1450 may also store communication instructions 1454 to facilitate communicating with one or more additional devices, one or more computers and/or one or more servers. Memory 1450 may include graphical user interface instructions 1456 to facilitate graphic user interface processing; sensor processing instructions 1458 to facilitate sensor-related processing and functions; phone instructions 1460 to facilitate phone-related processes and functions; electronic messaging instructions 1462 to facilitate electronic messaging-related process and functions; web browsing instructions 1464 to facilitate web browsing-related processes and functions; media processing instructions 1466 to facilitate media processing-related functions and processes; GNSS/Navigation instructions 1468 to facilitate GNSS and navigation-related processes and instructions; and/or camera instructions 1470 to facilitate camera-related processes and functions.

Memory 1450 may store application (or "app") instructions and data 1472, such as instructions for the apps described above in the context of FIGS. 1-12. Memory 1450 may also store other software instructions 1474 for various other software applications in place on device 1400.

In the foregoing specification, specific embodiments have been described. However, one of ordinary skill in the art appreciates that various modifications and changes can be made without departing from the scope of the invention as set forth in the claims below. For example, although the invention has been described and illustrated in connection with a school, it is not intended to be so limited. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

While various embodiments have been described above, it should be understood that they have been presented by way of example and not limitation. It will be apparent to persons skilled in the relevant art(s) that various changes in form and detail may be made therein without departing from the spirit and scope. In fact, after reading the above description, it will be apparent to one skilled in the relevant art(s) how to implement alternative embodiments. For example, other steps may be provided, or steps may be eliminated, from the described flows, and other components may be added to, or removed from, the described systems. Accordingly, other implementations are within the scope of the following claims.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112(f). Claims that do not expressly include the phrase "means for" or "step for" are not to be interpreted under 35 U.S.C. 112(f).

The invention claimed is:

1. A mobile defibrillator (AED) device comprising:
a mobile AED unit configured to operatively connect to a device capable of running an application, the application being configured to access at least one of a heartrate or blood oxygen saturation level of a subject measured by a wearable device worn by the subject during defibrillation, the mobile AED unit comprising one or more electrodes and being configured to measure breathing data for the subject;
wherein the device is configured to, via one or more processors executing on the device:
  detect a connection of the mobile AED unit to the device;
  detect that the one or more electrodes have been connected to the subject;
  receive electrocardiogram (EKG) measurements of the subject recorded by the electrodes;
  receive measured breathing data from the AED unit, the breathing data associated with breathing movements of a chest of the subject;
  receive, from the wearable device worn by the subject after the mobile AED unit has been connected to the device, wearable data measured by the wearable device and comprising at least one of the heartrate or the blood oxygen saturation level of the subject from a wearable device associated with the subject;
  analyze the breathing data to determine a breathing pattern of the subject;
  determine, based on the received EKG measurements, the wearable data comprising at least one of the heartrate or the blood oxygen saturation level, and the determined breathing pattern, that the subject requires an electrical shock;
  determine shock pattern factors based on the received EKG measurements, the wearable data comprising at least one of the heartrate or the blood oxygen saturation level and the determined breathing pattern, the shock pattern factors comprising a duration, a time interval, and an energy level; and
  administer the electrical shock to the subject using the determined shock pattern factors via the mobile AED based on the determining.

2. The AED device of claim 1, wherein determining that the subject requires an electrical shock comprises analyzing the EKG measurements and detecting a dangerous rhythm.

3. The AED device of claim 2, wherein detecting a dangerous rhythm comprises detecting at least one of rapid ventricular tachycardia or ventricular fibrillation.

4. The AED device of claim 1, wherein the device is further configured to:
  measure a current flowing between the one or more electrodes; and
  based on the measured current, display a recommendation for changing a distance between the one or more electrodes.

5. The AED device of claim 1 wherein determining, based on the received EKG measurements, the wearable data, and the determined breathing pattern, that the subject requires an electrical shock comprises:
  using a neural network with a plurality of nodes to map at least one of the EKG measurements, the wearable data, and the determined breathing pattern to shock pattern factors, the shock pattern factors comprising a duration, a time interval, and an energy level.

6. The AED device of claim 5, wherein the neural network is configured to estimate a likelihood that the subject will get return of spontaneous circulation (ROCS) based on the breathing data and the wearable data.

7. The AED device of claim 1, wherein receiving the EKG measurements comprises determining at least one of a pulse rate, a configuration of EKG-complexes, an ST elevation, a deprivation.

8. The AED device of claim 1, wherein administering the electrical shock to the subject comprises utilizing a power source of the device to power circuitry within the one or more electrodes.

* * * * *